(12) United States Patent
Hatanpaa et al.

(10) Patent No.: US 9,365,926 B2
(45) Date of Patent: Jun. 14, 2016

(54) PRECURSORS AND METHODS FOR ATOMIC LAYER DEPOSITION OF TRANSITION METAL OXIDES

(71) Applicant: ASM International N.V., Almere (NL)

(72) Inventors: Timo Hatanpaa, Espoo (FI); Jaakko Niinisto, Vantaa (FI); Mikko Ritala, Espoo (FI); Markku Leskela, Espoo (FI); Suvi Haukka, Helsinki (FI)

(73) Assignee: ASM International N.V. (NL)

( * ) Notice: Subject to any disclaimer, the term of this patent is extended or adjusted under 35 U.S.C. 154(b) by 0 days.

(21) Appl. No.: 14/629,333

(22) Filed: Feb. 23, 2015

(65) Prior Publication Data

US 2015/0191817 A1 Jul. 9, 2015

Related U.S. Application Data

(63) Continuation of application No. 13/034,564, filed on Feb. 24, 2011, now abandoned.

(60) Provisional application No. 61/308,263, filed on Feb. 25, 2010.

(51) Int. Cl.
| | |
|---|---|
| *C23C 16/40* | (2006.01) |
| *C23C 16/455* | (2006.01) |
| *C01G 23/07* | (2006.01) |
| *C01G 25/02* | (2006.01) |
| *C01G 27/02* | (2006.01) |

(52) U.S. Cl.
CPC ............. *C23C 16/405* (2013.01); *C01G 23/07* (2013.01); *C01G 25/02* (2013.01); *C01G 27/02* (2013.01); *C23C 16/45527* (2013.01); *C23C 16/45553* (2013.01); *C01P 2006/40* (2013.01)

(58) Field of Classification Search
None
See application file for complete search history.

(56) References Cited

U.S. PATENT DOCUMENTS

| | | | |
|---|---|---|---|
| 4,058,430 A | 11/1977 | Suntola et al. | |
| 4,927,670 A | 5/1990 | Erbil | |
| 5,225,561 A | 7/1993 | Kirlin et al. | |
| 5,439,876 A | 8/1995 | Graf et al. | |
| 5,453,494 A | 9/1995 | Kirlin et al. | |
| 5,472,927 A | 12/1995 | Mulder et al. | |
| 5,496,582 A | 3/1996 | Mizutani et al. | |

(Continued)

FOREIGN PATENT DOCUMENTS

| | | |
|---|---|---|
| EP | 344 352 B1 | 12/1989 |
| EP | 046 395 A1 | 7/1991 |
| FI | 108375 B | 1/2002 |

OTHER PUBLICATIONS

Gloeckner Organometallics 2009 v28 p. 5866-5876.*

(Continued)

*Primary Examiner* — Joseph Miller, Jr.
(74) *Attorney, Agent, or Firm* — Knobbe, Martens, Olson & Bear LLP

(57) ABSTRACT

Methods are provided herein for forming transition metal oxide thin films, preferably Group IVB metal oxide thin films, by atomic layer deposition. The metal oxide thin films can be deposited at high temperatures using metalorganic reactants. Metalorganic reactants comprising two ligands, at least one of which is a cycloheptatriene or cycloheptatrienyl (CHT) ligand are used in some embodiments. The metal oxide thin films can be used, for example, as dielectric oxides in transistors, flash devices, capacitors, integrated circuits, and other semiconductor applications.

23 Claims, 12 Drawing Sheets

(56) References Cited

U.S. PATENT DOCUMENTS

| | | | |
|---|---|---|---|
| 5,617,290 | A | 4/1997 | Kulwicki et al. |
| 5,711,811 | A | 1/1998 | Suntola et al. |
| 5,972,430 | A | 10/1999 | DiMeo et al. |
| 6,020,024 | A | 2/2000 | Maiti et al. |
| 6,087,257 | A | 7/2000 | Park et al. |
| 6,099,904 | A | 8/2000 | Mak et al. |
| 6,144,060 | A | 11/2000 | Park et al. |
| 6,380,579 | B1 | 4/2002 | Nam et al. |
| 6,420,230 | B1 | 7/2002 | Derderian et al. |
| 6,444,592 | B1 | 9/2002 | Ballantine et al. |
| 6,583,057 | B1 | 6/2003 | Alluri et al. |
| 6,780,704 | B1 | 8/2004 | Raaijmakers et al. |
| 6,800,567 | B2 | 10/2004 | Cho et al. |
| 7,491,347 | B2 | 2/2009 | Park et al. |
| 2001/0024387 | A1 | 9/2001 | Raaijmakers et al. |
| 2002/0142588 | A1 | 10/2002 | Basceri et al. |
| 2002/0153579 | A1 | 10/2002 | Yamamoto |
| 2003/0176047 | A1 | 9/2003 | Doan et al. |
| 2004/0125541 | A1 | 7/2004 | Chung |
| 2005/0089632 | A1 | 4/2005 | Vehkamaki et al. |
| 2005/0271813 | A1 | 12/2005 | Kher et al. |
| 2006/0157861 | A1 | 7/2006 | Park et al. |
| 2006/0292872 | A1 | 12/2006 | Haukka et al. |
| 2012/0323008 | A1 | 12/2012 | Barry et al. |

OTHER PUBLICATIONS

Cotton Annual Rep Prog Chem Sect A—Inorg Chem 2010 V106 p. 155-164.*
Tamm Organometallics 2005 V24 p. 3163-3171.*
Advances in Organometallic Chemistry, Ed. Stone and West, vol. 40, Academic Press (1996).
Alt, J. of Organometallic Chemistry, 391 (1990), p. 53-60 and English translation.
Bedair, S.M., "Atomic Layer Epitaxy Deposition Processes," J. Vac. Sci Technol. B 12(1), Jan./Feb. 1994, pp. 179-185.
Bilodeau et al., "MOCVD BaSrTiO3 for [3]1-Gbit DRAMs," Solid State Technology, pp. 235-242 (Jul. 1997).
Huang et al. "The surface morphology of atomic layer deposited magnesia", Journal of Materials Science Letters 12, pp. 1444-1446, Chapman & Hall (1993).
Huang et al., "Temperature-dependence of the growth orientation of atomic layer growth MgO", Appl. Phys. Lett. 61 (12); pp. 1450-1452 (Sep. 1992).
Huang, et al. "Preparation of Characterization of Thin Films of MgO, Al2O3 and MgAl2O4 by Atomic Layer Deposition", Journal of Electronic Materials, vol. 22, No. 2 (1993).
Iiskola, et al. "Functional surface groups for single-site heterogeneous ?-olefin polymerization catalysts", Applied Surface Science 121/122 , pp. 373-377, Elsevier Science B.V. (1997).
Kang et al., "Deposition Characteristics of (Ba, Sr) TiO3 Thin Films by Liquid Source Metal-Organic Chemical Vapor Deposition at Low Substrate Temperatures," Jpn. J. Appl. Phys., vol. 36, pp. 6946-6952 (1997).
Kiyotoshi et al., "Chemical Vapor Deposition of High Quality (Ba, Sr)TiO3 Thin Films Using Individual Vaporizing Liquid Source Supply System," Electrochemical Society Proceedings, vol. 97-25, pp. 1063-1070 (1997).
Martensson et al., "Halide chemical vapour deposition of Bi2Sr2CaCu2O8+x: aspects of epitaxy," Journal of Crystal Growth, vol. 156, pp. 67-73 (1995).

Musgrave et al., "Precursors for Atomic Layer Deposition of High-k Dielectrics", Future Fab Intl. Issue 18, Jan. 12, 2005.
Nakano et al., "Digital Chemical Vapor Deposition of SiO2," Appl. Phys. Lett. 57 (11), Sep. 10, 1990, pp. 1096-1098.
Niinistö et al., "Synthesis of oxide thin films and overlayers by atomic layer epitaxy for advanced applications," Materials Science & Engineering, vol. B41, pp. 23-29 (1996).
Niinisto et al., Abstract presented Jun. 23, 2010 at the 10th International Conference on Atomic Layer Deposition, Seoul, Korea.
Niinisto, J. of Applied Physics, vol. 95, No. 1 (Jan. 2004), p. 84.
Puurunen, R., "Surface chemistry of atomic later deposition: a case study for the trimethylaluminum/water process" Journal of Applied Physics, vol. 97 (2005):12, pp. 121301-121352, 2005.
Putkonen, et al. "Enhanced growth rate in atomic layer epitaxy deposition of magnesium oxide thin films", Journal of Materials Chemistry, pp. 1857-1861, The Royal Society of Chemistry (2000).
Putkonen, J. Mater. Chem., vol. 11, 2001, p. 3141-3147.
Ritala et al., "Atomic Layer Epitaxy Growth of Titanium Dioxide Thin Films from Titanium Ethoxide," Chem. Mater., vol. 6, pp. 556-561 (1994).
Ritala et al., "Growth of titanium dioxide thin films by atomic layer epitaxy," Thin Solid Films, vol. 225, pp. 288-295 (1993).
Ritala et al., "Titanium Is propoxide as a Precursor in Atomic Layer Epitaxy of Titanium Dioxide Thin Films," Chem. Mater., vol. 5, pp. 1174-1181 (1993).
Ritala, et al. "Atomic Layer Deposition", Handbook of Thin Film Materials, vol. 1: Deposition and Processes of Thin Films, Chapter 2, pp. 103-159, Academic Press (2002).
Schulz et al., "MOCVD Routes to Thin Metal Oxide Films for Superconducting Electronics," Adv. Mater., vol. 6, No. 10, pp. 719-730 (1994).
Schuisky, CVD, 2000, vol. 6, No. 3, pp. 140.
Sheppard, "Advances in Processing of Ferroelectric Thin Films," Ceramic Bulletin, vol. 71, No. 1, pp. 85-95 (1992).
Suntola, "Atomic Layer Epitaxy," Thin Solid Films, vol. 216, pp. 84-89 (1992).
Suntola, "Atomic Layer Epitaxy", Handbook of Crystal Growth 3, Thin Films and Epitaxy, Part B: Growth Mechanisms and Dynamics, Chapter 14, pp. 601-663, , Elsevier Science B. V. 1994.
Timmers et al., "An Advanced Inorganic Laboratory Experiment Using Synthesis and Reactivity of a Cycloheptatriene Molybdenum Complex," J. Chem. Ed., vol. 71, No. 11, 1994, pp. 987-990.
U.S. File History printed Feb. 21, 2012 for U.S. Appl. No. 09/787,062, filed Jun. 28, 2001, entitled "Method for Growing Oxide Thin Films Containing Barium and Strontium," (SEPP9.001APC).
U.S. File History printed Feb. 21, 2012 for U.S. Appl. No. 11/317,656, filed Dec. 22, 2005, entitled "Oxide Films Containing Titanium," (SEPP9.001CP1).
U.S. File History printed Feb. 21, 2012 for U.S. Appl. No. 11/864,677, filed Sep. 28, 2007, entitled "Metal Oxide Films," (SEPP9.001CP1C1).
Vehkamäki et al., "Growth of SrTiO3 and BaTiO3 Tin Films by Atomic Layer Deposition," Electrochemical and Solid-State Letters, 2 (10) pp. 504-506 (1999).
Wojtczak et al., "A Review of Group 2 (Ca, Sr, Ba) Metal-Organic Compounds as Precursors for Chemical Vapor Deposition," Advances in Organometallic Chemistry, vol. 40, pp. 215-340 Academic Press (1996).

* cited by examiner

|  | Zr | O | H | C | Zr/O |
|---|---|---|---|---|---|
| 300 c | 33+-1 | 66+-2 | 0.74+-0.25 | 0.38+-0.08 | 0.50 |
| 350 c | 33.5+-1.1 | 66.4+-2.4 | 0 | <0.06 | 0.50 |

FIG. 4 provide a first vapor phase reactant pulse comprising
a transition metal CHT reactant to the reaction chamber;

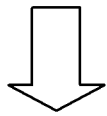

remove excess reactant from the
reaction chamber; if necessary

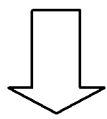

provide a second vapor phase reactant pulse comprising an oxygen
precursor

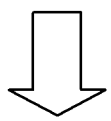

remove excess reactant and any reaction
byproducts from the reaction chamber

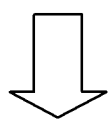

repeat providing and removing steps until a
transition metal oxide thin film of a desired thickness is formed

*FIG. 8*

PRECURSORS AND METHODS FOR ATOMIC LAYER DEPOSITION OF TRANSITION METAL OXIDES

REFERENCE TO RELATED APPLICATIONS

The present application is a continuation of U.S. non-provisional application Ser. No. 13/034,564, filed Feb. 24, 2011, which claims priority to U.S. provisional application No. 61/308,263, filed Feb. 25, 2010. The priority applications are hereby incorporated by reference in their entirety.

PARTIES OF JOINT RESEARCH AGREEMENT

The invention claimed herein was made by, or on behalf of, and/or in connection with a joint research agreement between the University of Helsinki and ASM Microchemistry Oy signed on Nov. 14, 2003 and renewed in 2008. The agreement was in effect on and before the date the claimed invention was made, and the claimed invention was made as a result of activities undertaken within the scope of the agreement.

BACKGROUND OF THE INVENTION

1. Field of the Invention

The present application relates generally to methods and compositions for depositing transition metal oxide thin films, such as titanium, zirconium and hafnium oxide thin films, by atomic layer deposition using metalorganic precursors. The metalorganic precursors comprise at least one cycloheptatriene (CHT) ligand.

2. Description of the Related Art

Atomic layer deposition (ALD) is a self-limiting process, whereby alternated pulses of reactants saturate a substrate surface. The deposition conditions and precursors are selected such that an adsorbed layer of precursor in one pulse leaves a surface termination that is non-reactive with the gas phase reactants of the same pulse. A subsequent pulse of different reactants reacts with the previous termination to enable continued deposition. Thus, each cycle of alternated pulses typically leaves no more than about one molecular layer of the desired material. The principles of ALD type processes have been presented by T. Suntola, e.g. in the Handbook of Crystal Growth 3, Thin Films and Epitaxy, Part B: Growth Mechanisms and Dynamics, Chapter 14, Atomic Layer Epitaxy, pp. 601-663, Elsevier Science B. V. 1994, the disclosure of which is incorporated herein by reference. Variations of ALD have been proposed that allow for modulation of the growth rate. However, to provide for high conformality and thickness uniformity, these reactions are still more or less self-saturating.

While ALD processes can be used to deposit films at lower temperatures, typically CVD processes have been used for higher temperature growth because the reactions occur more rapidly at higher temperatures. In addition, some ALD processes can lose their self limiting nature at high temperatures. In some cases, higher temperatures can cause undesirable decomposition of some precursors. Some precursor decomposition can disrupt the self limiting nature of the ALD process, for example if the products of the decomposition reaction react with each other and/or react with the adsorbed species to deposit material on the substrate surface.

Atomic layer deposition (ALD) of Group IVB metal oxides, such as $TiO_x$, $ZrO_2$ and $HfO_2$, has been studied for years. However, higher temperature ALD options for these metal oxides are quite limited. Metal halide reactants are typically used; however, metal halides are incompatible with some materials and processes. Some metal-organic precursors have also been used. However, these reactants have not been well suited for higher temperature deposition processes.

SUMMARY OF THE INVENTION

In accordance with one aspect of the present invention, methods for forming transition metal oxide thin films on a substrate in a reaction chamber by atomic layer deposition using metalorganic reactants are provided. Organometallic reactants are used in some embodiments. In some embodiments the transition metal oxide thin films are Group IVB metal oxide thin films. In some embodiments, the methods comprise providing a vapor phase pulse of a first reactant comprising a first Group IVB metalorganic precursor to a reaction chamber such that it forms no more than a monolayer on a substrate in the reaction chamber; removing excess first reactant from the reaction chamber; providing a vapor phase pulse of a second reactant comprising oxygen to the reaction chamber such that it converts the adsorbed Group IVB metal reactant to a metal oxide; and removing excess second reactant and any reaction byproducts from the reaction chamber. The providing and removing steps are repeated until a thin metal oxide film of a desired thickness and composition is obtained. The substrate temperature during the providing and removing steps may be above about 300° C., more preferably above about 350° C. In some embodiments the metalorganic precursor is an organometallic precursor, comprising a carbon-metal bond.

In accordance with another aspect of the present invention, methods for forming transition metal oxide films, preferably Group IVB metal oxide films, by atomic layer deposition comprise alternately and sequentially contacting a substrate with vapor phase pulses of a cycloheptatrienyl or cycloheptatriene (CHT) metal reactant and an oxygen source. The alternate and sequential pulses are repeated until a thin film of a desired thickness is obtained.

CHT metal reactants are metalorganic, typically organometallic compounds, comprising at least one chycloheptatrienyl or cycloheptatriene ligand (a CHT ligand). In some embodiments the CHT metal reactant comprises only two ligands, including at least one cycloheptatrienyl or cycloheptatriene (CHT) ligand. In some embodiments the CHT metal reactant comprises two CHT ligands. In some embodiments the CHT metal reactant comprises two cycloheptatrienyl ligands. In other embodiments the CHT metal reactant comprises one CHT ligand and one cyclopentadienyl ligand (Cp). In some embodiments, the CHT reactant does not comprise a halide. In some embodiments, the CHT reactant comprises one cycloheptadienyl (CHD) ligand. In some embodiments, the CHT reactant comprises two $C_7H_8$ cycloheptatriene ligands.

In some embodiments, a CHT metal reactant is selected from the group consisting of reactants of the formula:

$$R_xCp\text{-}M\text{-}CHT, \qquad (I)$$

where $R_xCp$ represents substituted or unsubstituted cyclopentadienyl, CHT is cycloheptatrienyl ($C_7H_7$) and M is selected from Ti, Zr and Hf In other embodiments, a CHT metal reactant is selected from the group consisting of reactants of the formula:

$$(R_1R_2R_3R_4R_5R_6R_7)CHT\text{-}M\text{-}Cp(R_8R_9R_{10}R_{11}R_{12}), \qquad (II)$$

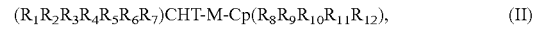

where M is selected from Ti, Zr and Hf, $R_{1\text{-}12}$ can independently be H or an alkyl group.

In other embodiments, a CHT metal reactant is selected from the group consisting of reactants of the formula:

$$(R_1R_2R_3R_4R_5R_6R_7)\text{CHT-M-CHT}$$
$$(R_8R_9R_{10}R_{11}R_{12}R_{13}R_{14}), \quad \text{(III)}$$

where M is selected from Ti, Zr and Hf, $R_{1-14}$ can independently be H or an alkyl group.

In other embodiments, a CHT metal reactant is selected from the group consisting of reactants of the formula:

$$R_1R_2R_3R_4R_5R_6R_7)\text{CHT-M-L}, \quad \text{(IV)}$$

where M is selected from Ti, Zr and Hf, $R_{1-7}$ can independently be H or an alkyl group and L is a mono or bidentate alkyl, cycloalkyl, alkoxy, amide or imido group. L may also be a acyclic or cyclic dienyl ligand.

In other embodiments, a CHT metal reactant is selected from the group consisting of reactants of the formula:

$$(R_1R_2R_3R_4R_5R_6R_7)\text{CHT-M-CHD}$$
$$(R_8R_9R_{10}R_{11}R_{12}R_{13}R_{14}R_{15}R_{16}), \quad \text{(V)}$$

where M is selected from Ti, Zr and Hf, $R_{1-16}$ can independently be H or an alkyl group and CHD is a cyloheptadienyl ($C_7H_9$).

In other embodiments a CHT reactant it is selected from the group consisting of reactants of the formula:

$$(R_1R_2R_3R_4R_5R_6R_7R_8)\text{X-M-X}$$
$$(R_9R_{10}R_{11}R_{12}R_{13}R_{14}R_{15}R_{16}), \quad \text{(VI)}$$

where M is selected from Ti, Zr and Hf, $R_{1-14}$ can independently be H or an alkyl group and X is cycloheptariene ($C_7H_8$).

In some embodiments, a CHT metal reactant can take different forms depending on the conditions. For example, in some embodiments a CHT metal reactant may have formula (V) under some conditions, but may be in the form of formula (VI) under other conditions.

In the formulas (I)-(VI) CHT, CHD or X, denote the structure of the ligand i.e. $C_7$ ring structure with double bonds or delocalized electrons, where different groups $R_1$-$R_{16}$ can attach. For example, according to formula (IV) the compound can be $C_7H_7$-M-L or $((CH_3)_3C_7H_4)$-M-L, not $H_7C_7H_7$-M-L or $(H_4(CH_3)_3C_7H_7)$-M-L, respectively.

In another aspect of the invention, transition metal nitride thin films, such as Group IVB metal nitride films, are deposited by ALD using a transition metal CHT reactant and a nitrogen containing reactant. In some embodiments the metal CHT reactant comprises two CHT ligands. In some embodiments the CHT reactant does not comprise a Cp group. In some embodiments, the CHT reactant comprises two $C_7H_8$ cycloheptatriene ligands.

In still another aspect of the invention, transition metal carbide thin films, such as Group IVB metal carbide films, are deposited by ALD using a metal CHT reactant. In some embodiments the metal CHT reactant comprises two CHT ligands. In some embodiments, the CHT reactant does comprise two $C_7H_8$ cycloheptatriene ligands.

In another aspect of the invention, methods of synthesizing transition metal precursors comprising one or more CHT ligands are provided. In some embodiments, methods of synthesizing $(C_7H_8)M(C_7H_8)$, where M is a transition metal, preferably a Group IVB metal, are provided. The methods may comprise forming a reaction mixture by combining a transition metal reactant with ferric chloride, cycloheptatriene and tetrhydrofuran (THF) in a flask containing magnesium chips. The transition metal reactant may be, for example, a Group IVB transition metal reactant, preferably a metal halide. Exemplary reactants include transition metal chlorides. In one embodiment, the transition metal reactant is $TiCl_4$.

These and other embodiments will become readily apparent to those skilled in the art from the following detailed description, the invention not being limited to any particular preferred embodiments disclosed.

Certain objects and advantages of the disclosed precursors and methods have been described herein. Of course, it is to be understood that not necessarily all such objects or advantages may be achieved in accordance with any particular embodiment. Thus, for example, those skilled in the art will recognize that the invention may be embodied or carried out in a manner that achieves or optimizes one advantage or group of advantages as taught herein without necessarily achieving other objects or advantages.

BRIEF DESCRIPTION OF THE DRAWINGS

FIG. 4 shows TofERDA data for $ZrO_2$ films deposited using (MeCp)ZrCHT and $O_3$ at various temperatures.

FIG. 8 is a flow chart of an embodiment of an ALD process for depositing a Group IVB metal oxide using a CHT metal precursor.

DETAILED DESCRIPTION OF THE PREFERRED EMBODIMENT

Figures 1A, 1B:
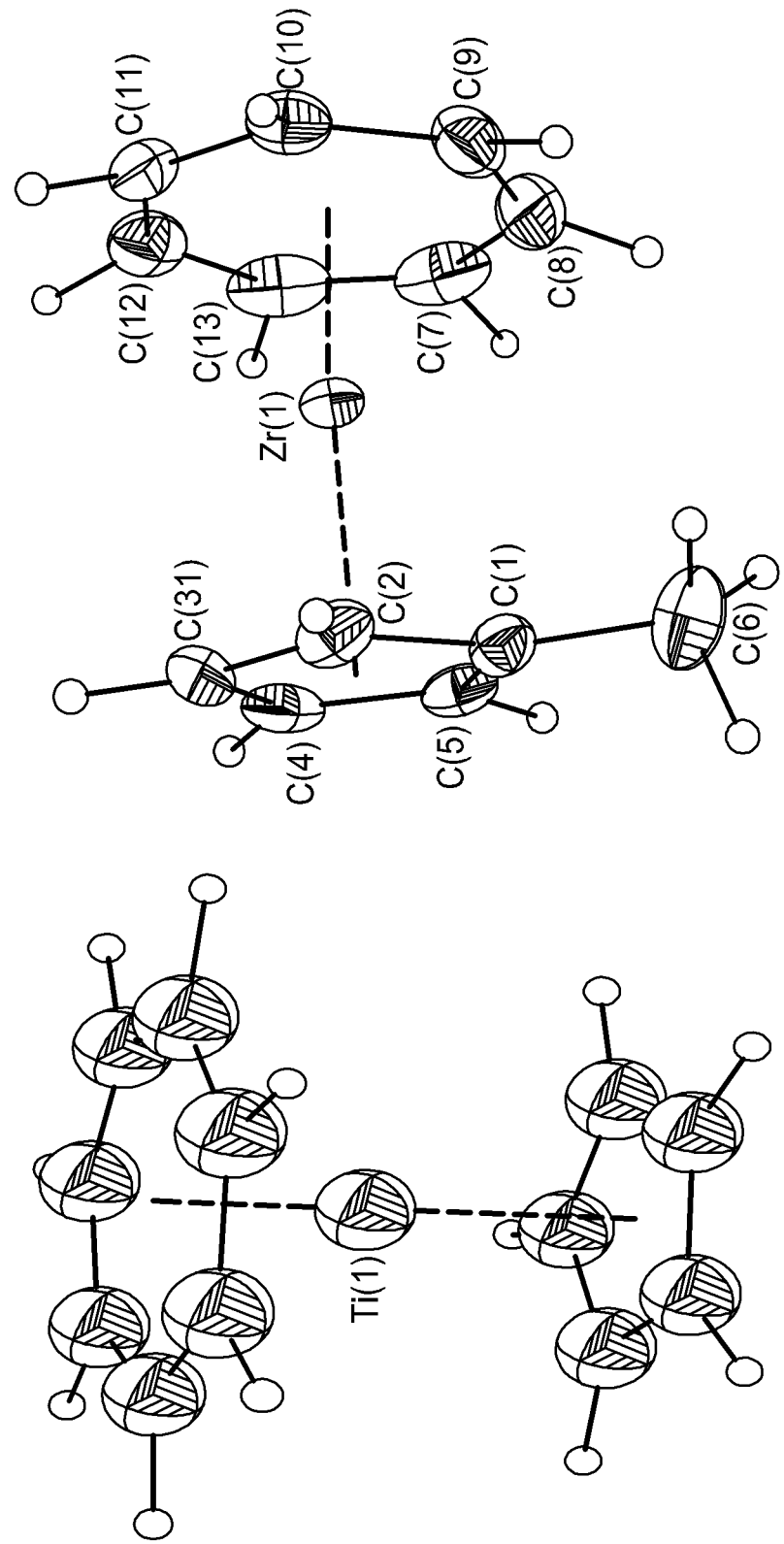
FIGS. 1A and 1B show the structure of CpTiCHT (FIG. 1A) and (MeCp)ZrCHT (FIG. 1B).

Methods and compositions for forming transition metal oxide films using metalorganic precursors are described herein. While primarily illustrated in the context of forming Group IVB metal oxide films, other transition metals can be substituted for the Group IVB metals in some embodiments, as will be recognized by the skilled artisan. In addition, although the thin films are generally described with respect to the formation of an integrated circuit, such as a capacitor or transistor, the skilled artisan will readily appreciate the application of the principles and advantages disclosed herein to various contexts in which metal oxide thin films are useful. For example, transparent titanium oxide films can be used in flat panel displays, LEDs, and solar cells.

In addition, although illustrated primarily in terms of deposition of transition metal oxide thin films, in some embodiments transition metal nitride or metal carbide films, such as Group IVB metal nitride and carbide films, can be deposited by ALD using the disclosed metal precursors.

As used herein, the term metal oxide film refers to a transition metal oxide film unless otherwise stated. Preferred transition metal oxide films are Group IVB metal oxide films. Group IVB metal oxide thin films include oxide films comprising titanium (Ti), zirconium (Zr) and/or hafnium (Hf). Exemplary Group IVB metal oxide films that are specifically discussed herein include $TiO_2$, $ZrO_2$ and $HfO_2$. Other Group IVB metal oxide films will be apparent to the skilled artisan. In addition, as noted above, in some embodiments the Group IVB metals can be substituted with other transition metals, as will be understood by the skilled artisan.

In some embodiments, transition metal oxide films are deposited on a substrate by atomic layer deposition (ALD) type processes utilizing one or more metalorganic precursors. In some embodiments the metalorganic precursor is an organometallic precursor and thus comprises a carbon-metal bond. As discussed below, in some embodiments deposition temperatures of greater than 300° C. are used. In other embodiments, deposition temperatures of greater than 350° C. are used.

In particular embodiments, CHT metal reactants are utilized. CHT metal reactants are metal reactants comprising at least one CHT ligand. The CHT metal reactant may be a metalorganic compound and in some embodiments is an organometallic compound. CHT ligands are cycloheptatrienyl and cycloheptatriene ligands. Thus, CHT metal reactants comprise at least one cycloheptatrienyl ligand or, in some cases, at least one cycloheptatriene ligand. The CHT metal reactants used herein typically comprise only two ligands, one of which is a CHT ligand (cycloheptatrienyl or cycloheptatriene). In some embodiments, the reactants comprise either two CHT ligands or one CHT ligand and one cyclopentadienyl (Cp) ligand. In some embodiments the CHT reactant comprises two cycloheptatrienyl ligands. In some embodiments, the CHT reactant comprises two $C_7H_8$ cycloheptatriene ligands. In other embodiments the CHT metal reactants comprise one CHT ligand and another ligand such as a mono or bidentate alkyl, cycloalkyl, alkoxy, amide or imido group. In other embodiments the CHT metal reactants comprise one CHT ligand and another ligand such as a dienyl ligand. In some embodiments the CHT metal reactant comprises a transition metal. However, the CHT metal reactants typically comprise one or more Group IVB metals. In some embodiments, the CHT reactants do not comprise a halide.

In some embodiments, CHT metal reactants have the general formula:

$$R_xC_p\text{-}M\text{-}CHT, \quad (I)$$

where $R_xCp$ represents substituted or unsubstituted cyclopentadienyl, CHT is cycloheptatrienyl ($C_7H_7$) and M is selected from Ti, Zr and Hf In other embodiments, CHT metal reactants have the general formula:

$$(R_1R_2R_3R_4R_5R_6R_7)CHT\text{-}M\text{-}Cp(R_8R_9R_{10}R_{11}R_{12}), \quad (II)$$

where M is selected from Ti, Zr and Hf, $R_{1\text{-}12}$ can independently be H or an alkyl group, and may be a bridged or substituted alkyl. Exemplary alkyl groups include, but are not limited to Me, Et, Pr, $^iPr$, Bu, $^tBu$ and other $C_1$-$C_{10}$ alkyls. Other alkyl groups that may be used will be apparent to the skilled artisan.

In still other embodiments, the CHT metal reactants have the general formula:

where M is selected from Ti, Zr and Hf, $R_{1\text{-}14}$ can independently be H or an alkyl group, and may be a bridged or substituted alkyl. Exemplary alkyl groups include, but are not limited to Me, Et, Pr, $^iPr$, Bu, $^tBu$ and other $C_1$-$C_{10}$ alkyls. Other alkyl groups that may be used will be apparent to the skilled artisan.

In still other embodiments, the CHT metal reactants have the general formula:

$$(R_1R_2R_3R_4R_5R_6R_7)CHT\text{-}M\text{-}L, \quad (IV)$$

where M is selected from Ti, Zr and Hf $R_{1\text{-}7}$ can independently be H or an alkyl group, and may be a bridged or substituted alkyl; and L is either a mono or bidentate alkyl, cycloalkyl, alkoxy, amide or imido group. L may also be a acyclic or cyclic dienyl ligand. Exemplary alkyl groups include, but are not limited to Me, Et, Pr, $^iPr$, Bu, $^tBu$ and other $C_1$-$C_{10}$ alkyls. Other alkyl groups that may be used will be apparent to the skilled artisan. Exemplary alkoxy groups include OMe, OEt, $O^1Pr$, $O^tBu$, $O_2CMe$ and $O_2C^tBu$. Exemplary amide groups include $N(Me)_2$, $N(MeEt)$ and $N(Et)_2$. Exemplary dienyl ligands include 2,4-dimethylpenta-1,4-dienyl and hepta-2,5-dienyl.

In other embodiments, a CHT metal reactant is selected from the group consisting of reactants of the formula:

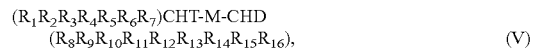

where M is selected from Ti, Zr and Hf; $R_{1\text{-}16}$ can independently be H or an alkyl group, and may be a bridged or substituted alkyl. Exemplary alkyl groups include, but are not limited to Me, Et, Pr, $^iPr$, Bu, $^tBu$ and other $C_1$-$C_{10}$ alkyls. Other alkyl groups that may be used will be apparent to the skilled artisan. CHD is a cyloheptadiene ($C_7H_9$).

In other embodiments, a CHT metal reactant is selected from the group consisting of reactants of the formula:

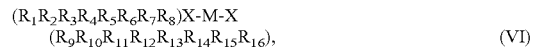

where M is selected from Ti, Zr and Hf; $R_{1\text{-}16}$ can independently be H or an alkyl group, and may be a bridged or substituted alkyl. Exemplary alkyl groups include, but are not limited to Me, Et, Pr, $^iPr$, Bu, $^tBu$ and other $C_1$-$C_{10}$ alkyls. Other alkyl groups that may be used will be apparent to the skilled artisan. X is cycloheptatriene ($C_7H_8$).

In some embodiments, a CHT metal reactant can take different forms depending on the conditions. For example, in some embodiments a CHT metal reactant may have formula (V) under some conditions, but may be in the form of formula (VI) under other conditions.

In the formulas (I)-(VI) CHT, CHD or X, denote the structure of ligand i.e. $C_7$ ring structure with double bonds or delocalized electrons, where different groups $R_1$-$R_{16}$ can attach. For example, according to formula (IV) the compound can be $C_7H_7$-M-L or $((CH_3)_3C_7H_4)$-M-L, not $H_7C_7H_7$-M-L or $(H_4(CH_3)_3C_7H_7)$-M-L, respectively.

In some embodiments one or more of the alkyl groups in $R_1$-$R_{16}$ mentioned in formulas (I)-(VI) may be $C_1$-$C_2$ alkyls, such as Me or Et, while in other embodiments one or more of the alkyl groups in $R_1$-$R_{16}$ mentioned in formulas (I)-(VI) may be $C_3$-$C_{10}$ alkyls, such as Pr, $^iPr$, Bu and $^tBu$.

In some embodiments one or more of the $R_1$-$R_{14}$ substituents mentioned in formulas (I)-(VI) are other than hydrogen. In yet other embodiments two or more of the $R_1$-$R_{14}$ substituents mentioned in formulas (I)-(VI) are other than hydrogen. In yet other embodiments three or more of the $R_1$-$R_{16}$ substituents mentioned in formulas (I)-(VI) are other than hydrogen.

FIG. 1 illustrates the structures of two exemplary reactants, CpTiCHT and (MeCp)ZrCHT.

Atomic Layer Deposition Processes

ALD processes are generally based on controlled, self-limiting surface reactions of precursor chemicals. Gas phase reactions are avoided by feeding the precursors alternately and sequentially into the reaction chamber. Vapor phase reactants are separated from each other in the reaction chamber, for example, by removing excess reactants and/or reactant byproducts from the reaction chamber between reactant pulses.

Briefly, a substrate is loaded into a reaction chamber and is heated to a suitable deposition temperature, generally at lowered pressure. Deposition temperatures are typically maintained below the thermal decomposition temperature of the reactants but at a high enough level to avoid condensation of reactants and to provide the activation energy for the desired surface reactions. However, in some embodiments some minor decomposition may take place without significantly disrupting the step coverage and uniformity of the ALD process. Of course, the appropriate temperature window for any given ALD reaction will depend upon a variety of factors, including without limitation the surface termination and the particular reactant species involved.

In some embodiments, thin films are deposited at deposition temperatures of about 100 to about 500° C., more preferably about 150 to about 400° C. and in some embodiments about 300 to about 400° C. Particular deposition temperatures for some specific embodiments are provided below.

In some embodiments, metal oxide films are deposited on a substrate by atomic layer deposition (ALD) type processes utilizing one or more metalorganic precursors at temperatures greater than about 300° C. or at temperatures greater than about 350° C. In some of these embodiments, the metalorganic precursors are organometallic precursors. In some embodiments the precursors are metal CHT precursors as described herein.

A first transition metal reactant is conducted or pulsed into the chamber in the form of vapor phase pulse and contacted with the surface of the substrate. Conditions are preferably selected such that no more than about one monolayer of the first reactant is adsorbed on the substrate surface in a self-limiting manner. Excess first reactant and reaction byproducts, if any, are removed from the reaction chamber, such as by purging with an inert gas. The appropriate pulsing and purging times can be readily determined by the skilled artisan based on the particular circumstances.

Purging the reaction chamber means that vapor phase precursors and/or vapor phase byproducts are removed from the reaction chamber such as by evacuating the chamber with a vacuum pump and/or by replacing the gas inside the reactor with an inert gas such as argon or nitrogen. Typical purging times are from about 0.05 to 20 seconds, more preferably between about 0.5 and 10, and still more preferably between about 1 and 5 seconds. However, other purge times can be utilized if necessary, such as where highly conformal step coverage over extremely high aspect ratio structures or other structures with complex surface morphology is needed. Also, batch ALD reactors can utilize longer purging times because of increased volume and surface area.

A second gaseous reactant is pulsed into the chamber where it reacts with the first reactant bound to the surface. Excess second reactant and gaseous byproducts of the surface reaction are removed from the reaction chamber, preferably by purging with the aid of an inert gas and/or evacuation. The steps of pulsing and purging are repeated until a thin film of the desired thickness has been formed on the substrate, with each cycle leaving typically less than or no more than a molecular monolayer. The second reactant may be, for example, an oxygen containing reactant, such that a metal oxide is formed. In other embodiments the second reactant may comprise nitrogen or carbon, in order to form metal nitrides or metal carbides, respectively.

As mentioned above, each pulse or phase of each cycle is preferably self-limiting. An excess of reactants is supplied in each phase to saturate the susceptible structure surfaces. Surface saturation ensures reactant occupation of all available reactive sites (subject, for example, to physical size or "steric hindrance" restraints) and thus ensures excellent step coverage. However, in some embodiments, some minor non-self-limiting deposition may occur which does not significantly disturb the unique properties of ALD process.

According to some embodiments, a transition metal oxide thin film, preferably a Group IVB metal oxide thin film, is formed on a substrate by an ALD type process comprising multiple metal oxide deposition cycles, each metal oxide deposition cycle comprising:

providing a first vapor phase reactant pulse comprising a first metalorganic reactant to the reaction chamber such that it forms no more than a monolayer on the substrate, wherein the metalorganic reactant comprises a transition metal, preferably a Group IVB metal;

removing excess first reactant from the reaction chamber;

providing a second vapor phase reactant pulse comprising a second reactant to the reaction chamber, wherein the second reactant comprises oxygen; and removing excess second reactant and any reaction byproducts from the reaction chamber.

The providing and removing steps are repeated until a thin film of a desired thickness and composition is obtained. In some embodiments, the deposition cycle is carried out at a temperature of at least 300° C. or even at least 350° C.

Further, in some embodiments the metalorganic reactant is an organometallic reactant.

In some embodiments the same metalorganic precursor is utilized in each cycle. However, in other embodiments, different reactants can be utilized in one or more different cycles. In addition, the ALD process may begin with any phase of the deposition cycle.

In one embodiment illustrated in FIG. 8, a vapor phase reactant pulse comprising a Group IVB metal CHT reactant is provided to the reaction chamber where it contacts a substrate. Preferably the reactant is selected such that if it decomposes at the given process conditions it does not adversely affect the deposition process. Preferably the metal reactant comprises one or more of Ti, Hf, and Zr. In some embodiments, reactants are selected from the reactants of formula's (I), (II), (III), (IV), (V) and (VI).

Preferably, the metal CHT reactant is provided such that it forms no more than about a single molecular layer on the substrate. If necessary, any excess metal reactant can be purged or removed from the reaction space. In some embodiments, the purge step can comprise stopping the flow of metal reactant while still continuing the flow of an inert carrier gas such as nitrogen or argon.

Next, a vapor phase reactant pulse comprising an oxygen source or precursor is provided to the substrate and reaction chamber. Any of a variety of oxygen precursors can be used, including, without limitation: oxygen, plasma excited oxygen, atomic oxygen, ozone, water, nitric oxide (NO), nitrogen dioxide ($NO_2$), nitrous oxide ($N_2O$), hydrogen peroxide ($H_2O_2$), etc. A suitable oxygen precursor can be selected by the skilled artisan such that it reacts with the molecular layer of the metal reactant on the substrate to form a metal oxide under the particular process conditions. In some embodiments, ozone is used with a metal CHT reactant.

The oxygen source may be an oxygen-containing gas pulse and can be a mixture of an oxygen precursor and inactive gas, such as nitrogen or argon. In some embodiments the oxygen source may be a molecular oxygen-containing gas pulse. One source of oxygen may be air. In some embodiments, the oxygen source or precursor is water. In some embodiments the oxygen source comprises an activated or excited oxygen species. In some embodiments the oxygen source comprises ozone. The oxygen source may be pure ozone or a mixture of ozone and another gas, for example an inactive gas such as nitrogen or argon. In other embodiments the oxygen source is oxygen plasma.

The oxygen precursor pulse may be provided, for example, by pulsing ozone or a mixture of ozone and another gas into the reaction chamber. In other embodiments, ozone (or other oxygen precursor) is formed inside the reactor, for example by conducting oxygen containing gas through an arc. In other embodiments an oxygen containing plasma is formed in the reactor. In some embodiments the plasma may be formed in situ on top of the substrate or in close proximity to the substrate. In other embodiments the plasma is formed upstream of the reaction chamber in a remote plasma generator and plasma products are directed to the reaction chamber to contact the substrate. As will be appreciated by the skilled artisan, in the case of remote plasma the pathway to the substrate can be optimized to maximize electrically neutral species and minimize ion survival before reaching the substrate.

Each metal oxide deposition cycle typically forms no more than about one molecular layer of metal oxide. If necessary, any excess reaction byproducts or oxygen precursor can be removed from the reaction space. In some embodiments, the purge step can comprise stopping the flow of oxygen precursor while still continuing the flow of an inert carrier gas such as nitrogen or argon. Preferably the oxygen precursor has a decomposition temperature above the substrate temperature during deposition. In some embodiments the oxygen precursor may decompose at the substrate deposition temperature but does not disrupt the self limiting nature of the ALD process.

The metal oxide deposition cycle is typically repeated a predetermined number of times 150 to form a metal oxide of the desired thickness and composition. In some embodiments, multiple molecular layers of metal oxide are formed by multiple deposition cycles. In other embodiments, a molecular layer or less of metal oxide is formed.

Removing excess reactants can include evacuating some of the contents of the reaction space or purging the reaction space with argon, helium, nitrogen or any other inert gas. In some embodiments purging can comprise turning off the flow of the reactive gas while continuing to flow an inert carrier gas to the reaction space.

The precursors employed in the ALD type processes may be solid, liquid or gaseous material under standard conditions (room temperature and atmospheric pressure), provided that the precursors are in vapor phase before it is conducted into the reaction chamber and contacted with the substrate surface. "Pulsing" a vaporized precursor onto the substrate means that the precursor vapor is conducted into the chamber for a limited period of time. Typically, the pulsing time is from about 0.05 to 10 seconds. However, depending on the substrate type and its surface area, the pulsing time may be even higher than 10 seconds. Preferably, for a 300 mm wafer in a single wafer ALD reactor, a metal precursor, such as a Ti, Hf, or Zr precursor, is pulsed for from 0.05 to 20 seconds, more preferably for from 0.1 to 10 seconds and most preferably for about 0.3 to 5.0 seconds. An oxygen-containing precursor is preferably pulsed for from about 0.05 to 10 seconds, more preferably for from 0.1 to 5 seconds, most preferably for from about 0.2 to 3.0 seconds. However, pulsing times can be on the order of minutes in some cases, for example, if the process is applied to reactors having large surface area, such batch ALD reactors. The optimum pulsing time can be readily determined by the skilled artisan based on the particular circumstances.

The mass flow rate of the precursors can also be determined by the skilled artisan. In one embodiment, for deposition on 300 mm wafers the flow rate of metal precursors is preferably between about 1 and 1000 sccm without limitation, more preferably between about 100 and 500 sccm. The mass flow rate of the metal precursors is usually lower than the mass flow rate of the oxygen source, which is usually between about 10 and 10000 sccm without limitation, more preferably between about 100-2000 sccm and most preferably between 100-1000 sccm.

The pressure in the reaction chamber is typically from about 0.01 to about 20 mbar, more preferably from about 1 to about 10 mbar. However, in some cases the pressure will be higher or lower than this range, as can be readily determined by the skilled artisan. Atmospheric pressure could also be used for these high temperature reactions.

Before starting the deposition of the film, the substrate is typically heated to a suitable growth temperature. Growth temperatures are described above and typically range from about 100 to about 400° C. In some embodiments growth temperatures of greater than 300° C. or even 350° C. are used.

The deposition cycles can be repeated a predetermined number of times or until a desired thickness is reached. Preferably, the thin films are between about 5 Å and 200 nm thick, more preferably between about 10 Å and 100 nm thick.

In other embodiments, transition metal nitride thin films are deposited using a transition metal CHT reactant, preferably a Group IVB metal CHT reactant. The reaction conditions can be essentially as described above for deposition of transition metal oxide, except that a nitrogen-containing reactant is used in place of the oxygen reactant. Nitrogen containing reactants may be, for example, $NH_3$, nitrogen plasma, $N_2H_2$, hydrogen azide, hydrazine and/or hydrazine derivatives, amines, nitrogen radicals, and other excited species of nitrogen.

In other embodiments, transition metal carbide thin films are deposited using a transition metal CHT reactant, preferably a Group IVB metal CHT reactant. Again, the reaction conditions can be essentially as described above for deposition of transition metal oxides, except that a carbon-containing reactant is used in place of the oxygen reactant. In some embodiments, the carbon source is a hydrocarbon such as an alkane, alkene, and/or alkyne.

Deposition of Thin Films Comprising Zirconium Oxide

In some embodiments, methods are provided for depositing thin films comprising zirconium oxide. A vapor phase pulse of a zirconium CHT precursor is provided to the reaction chamber. The zirconium precursor may be selected from the group consisting of the compounds of formulas (I), (II), (III), (IV), (V) and (VI) above, where M is Zr. In some embodiments the precursor is (MeCp)ZrCHT. The zirconium precursor can be provided such that it forms no more than one monolayer of material on the substrate. Next, a vapor phase reactant pulse comprising an oxygen precursor is provided to the reaction chamber. The oxygen precursor can be provided such that it reacts with the zirconium precursor on the substrate surface. Preferred oxygen precursors include atomic oxygen, oxygen plasma, $O_2$, $H_2O$, $O_3$, NO, $NO_2$, $N_2O$, and $H_2O_2$. In some embodiments the oxygen precursor is $O_3$. Preferably the substrate temperature during pulses of zirconium and oxygen precursors is above about 300° C. The cycle can be generally referred to as a zirconium oxide deposition cycle. The deposition cycle can be repeated until the thin film reaches the desired thickness.

The process conditions for the zirconium oxide deposition can be essentially as described above in reference to the metal oxide deposition cycle.

Deposition of Thin Films Comprising Titanium Oxide

In some embodiments, methods are provided for depositing thin films comprising titanium oxide. A vapor phase pulse of a titanium CHT precursor is provided to the reaction chamber. The titanium precursor may be selected from the group consisting of the compounds of formulas (I), (II), (III), (IV), (V) and (VI) above, where M is Ti. In some embodiments the precursor is CpTiCHT. The titanium precursor can be provided such that it forms no more than one monolayer of material on the substrate. Next, a vapor phase reactant pulse comprising an oxygen precursor is provided to the reaction chamber. The oxygen precursor can be provided such that it reacts with the titanium precursor on the substrate surface. Preferred oxygen precursors include atomic oxygen, oxygen plasma, $O_2$, $H_2O$, $O_3$, NO, $NO_2$, $N_2O$, and $H_2O_2$. In some embodiments the oxygen precursor is $O_3$. Preferably the substrate temperature during pulses of titanium and oxygen precursors is above about 300° C. The cycle can be generally referred to as a titanium oxide deposition cycle. The deposition cycle can be repeated until the thin film reaches the desired thickness.

The process conditions for the titanium oxide deposition can be essentially as described above in reference to the metal oxide deposition cycle.

Deposition of Thin Films Comprising Hafnium Oxide

In some embodiments, methods are provided for depositing thin films comprising hafnium oxide. A vapor phase pulse of a hafnium CHT precursor is provided to the reaction chamber. The hafnium precursor may be selected from the group consisting of the compounds of formulas (I), (II), (III), (IV), (V) and (VI) above, where M is Hf. The hafnium precursor can be provided such that it forms no more than one monolayer of material on the substrate. Next, a vapor phase reactant pulse comprising an oxygen precursor is provided to the reaction chamber. The oxygen precursor can be provided such that it reacts with the hafnium precursor on the substrate surface. Preferred oxygen precursors include atomic oxygen, oxygen plasma, $O_2$, $H_2O$, $O_3$, NO, $NO_2$, $N_2O$, and $H_2O_2$. In some embodiments the oxygen precursor is $O_3$. Preferably the substrate temperature during pulses of hafnium and oxygen precursors is above about 300° C. The cycle can be generally referred to as a hafnium oxide deposition cycle. The deposition cycle can be repeated until the thin film reaches the desired thickness.

The process conditions for the hafnium oxide deposition can be essentially as described above in reference to the metal oxide deposition cycle.

Applications

Metal oxide films may be used, for example, as dielectric layers between top and bottom electrodes in capacitors. In some embodiments, a capacitor suitable for use in an integrated circuit is formed by a method comprising:

depositing a bottom electrode;

depositing a dielectric oxide layer over the bottom electrode by an atomic layer deposition process comprising alternating and sequential pulses of a metal CHT source and pulses of an oxygen source as described herein; and depositing a top electrode directly over and contacting the dielectric layer.

The metal oxides can also be used as dielectric layers in transistors. In one embodiment of a method for forming a transistor in an integrated circuit, a dielectric oxide layer is first deposited over one or more gate electrodes on a substrate by an ALD process. The deposition of the dielectric oxide layer can include any of the methods described herein. Preferably the dielectric oxide layer comprises one or more of hafnium, zirconium, and titanium. Next, a semiconductor is deposited on the dielectric oxide layer. In some embodiments the semiconductor comprises one or more of silicon and germanium. Next, electrically conductive source and drain electrodes are deposited on top of the semiconductor such that the drain electrodes align with the gate electrodes.

The skilled artisan will appreciate that the metal oxide thin films described herein have many other uses, such as a floating gate dielectric layer in a flash device, as a blocking oxide in charge trapping flash devices, as a gate dielectric in memory stacks, as a dielectric oxide in other semiconductor devices, etc. The thin films described herein can also be useful in optical areas, for example, titanium dioxide can be a transparent conducting oxide used in optical components, flat panel displays, LEDs, solar cells and chemical sensors.

Precursor Synthesis

Methods are also provided for synthesizing the metal CHT precursors used in the ALD processes described herein. In particular, CHT precursors of formulas (I), (II), (III), (IV), (V) and (VI) above, can be synthesized.

In some embodiments the CHT precursor that is synthesized is CpTiCHT and in other embodiments the precursor (MeCp)ZrCHT is synthesized, as described in the Examples below.

In other embodiments, transition metal precursors of formula (III) are synthesized, such as $(C_7H_8)M(C_7H_8)$, where M is a transition metal, preferably a group IVB metal such as Ti, Zr, Hf. In a container containing magnesium chips, anhydrous $FeCl_3$, cycloheptatriene, and tetrahydrofuran (THF) are combined. A transition metal precursor, such as a transition metal halide THF adduct is added to the reaction mixture, preferably over a long period of time and while stirring. The reaction is exothermic thus, for example, the transition metal precursor may be added over a 1-h period to avoid possible overheating of the stirred reaction mixture. The transition metal precursor comprises a Group IVB metal in some embodiments, and may be, for example, a transition metal chloride. The transition metal precursor may be in solution, such as in solution with THE The mixture may be stirred over night, for example at room temperature. Following stirring, the volatile products may be evaporated under vacuum.

Synthesis of $C_7H_8$—Ti—$C_7H_8$ using $TiCl_4$ is described in Example 8 below.

EXAMPLES

All complex preparations were done under exclusion of air and moisture using standard Schlenk and glove box techniques. Toluene and xylene were dried and stored over 4 Å molecular sieves. THF was freshly distilled from sodium benzophenone ketyl. Anhydrous Zirconium(IV) chloride (Aldrich 99.999%), Titanium(IV) chloride (Fluka >99.0%), Dicyclopentadienyl Titanium(IV) dichloride (Aldrich 97%), ferric chloride (Riedel-de Haën), magnesium turnings and cycloheptariene (Aldrich 90%) were used as received. Methylcyclopentadiene dimer was cracked to corresponding monomer just before usage.

$^1H$ and $^{13}C$ NMR spectra were recorded with a Varian Gemini 2000 instrument at ambient temperature. Chemical shifts were referenced to $SiMe_4$ and are given in ppm. Thermogravimetric analyses were carried out on a Mettler Toledo Star$^e$ system equipped with a TGA 850 thermobalance using a flowing nitrogen atmosphere at 1 atm. The heating rate was 10 ° C./min and the weights of the samples prepared to 70 μl pans were between 10-11 mg. Melting points were taken from the SDTA data measured by the thermobalance. Mass spectra were recorded with a JEOL JMS-SX102 operating in electron impact mode (70 eV) using a direct insertion probe and sublimation temperature range of 50-370° C.

Example 1

Synthesis of $(C_5H_5)Ti(C_7H_7)$

The synthesis was done using the method of Demerseman et al. (Inorg. Chem. 1982, 21, 3942.). CpTiCl$_3$ had to be synthesized initially and two different methods were employed synthesizing different batches. First the method of Sloan at al. (J. Am. Chem. Soc. 1959, 81, 1364.) was employed. The method of Hitchcock et al. (Dalton Trans., 1999, 1161.) was also used as Cp$_2$TiCl$_2$ is readily available.

In a 1-L flask containing 20 g of magnesium chips were added 2 g of anhydrous FeCl$_3$, 50 ml of cycloheptatriene, 50 ml of THF, and, over a 3-h period to allow the warming of the stirred reaction mixture, a solution of 57.45 g (0.26 mol) of CpTiCl3 in 400 ml of THF. The mixture was stirred at room temperature over night and the volatile products were evaporated under vacuum. Sublimation of the residue (130° C./0.05 mmHg) gave a blue solid: 85.8% yield (45.9 g); $^1$H NMR $(C_6D_6)$:), 4.91 (s, 5H, CH), 5.43 (s, 7H, CH); $^{13}C\{^1H\}$ NMR $(C_6D_6)$: 97.35 (CH, C$_7$-ring), 86.71 (CH, Cp ring); MS (EL 70 eV) m/z: 204 (M$^+$) with the correct isotopic distribution.

Figure 2:
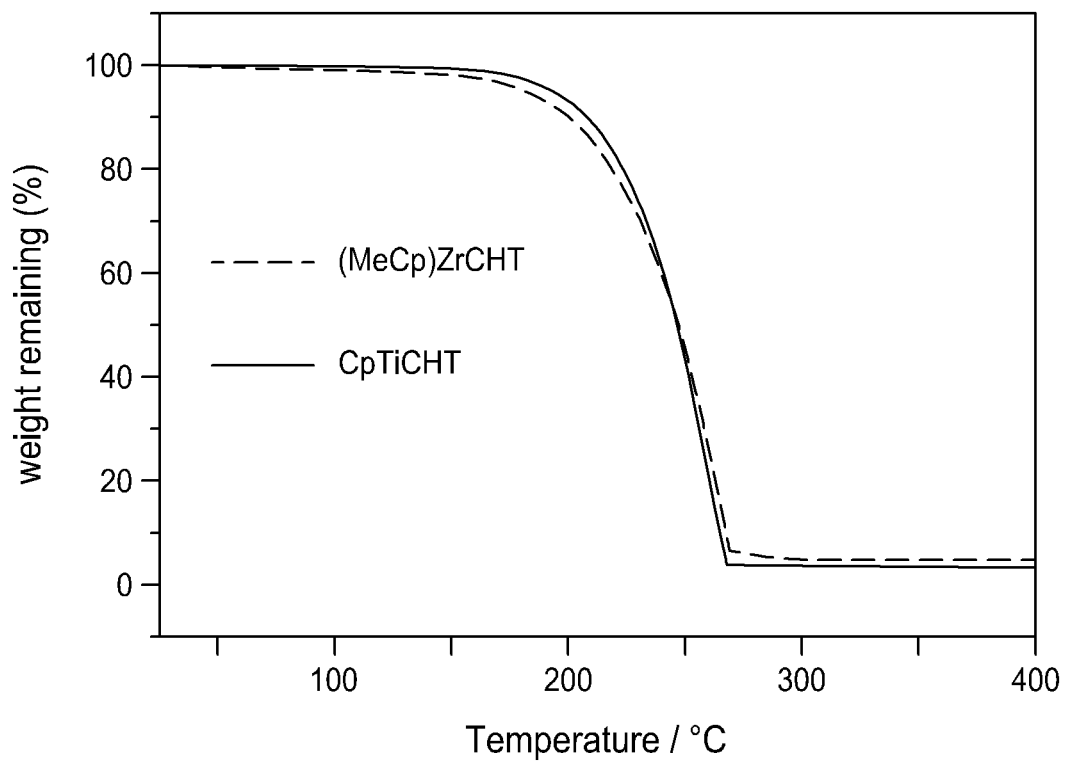
FIG. 2 shows the TGA curves measured for CpTiCHT and (MeCp)ZrCHT.

FIG. 1 shows the structure of CpTiCHT and FIG. 2 provides the TGA curve measured for CpTiCHT.

Example 2

Synthesis of $(MeC_5H_4)Zr(C_7H_7)$

The synthesis was performed in a fashion similar to that described for CpZrCHT by Tamm et al. (*Organometallics* 2005, 3163.). The method is also similar with that presented for CpTiCHT in Example 1 above. MeCpZrCl$_3$ needed in the synthesis was synthesized using the method of Hitchcock et al. (*Polyhedron* 1995, 14, 2745.). A Schlenk flask was charged with magnesium turnings (6 g, 247 mmol), catalytic amounts of ferric chloride (0.6 g, 3.7 mmol), cycloheptatriene (15 ml), and THF (50 ml). This reaction mixture was treated dropwise with a solution of MeCpZrCl$_3$ (17.3 g, 62.4 mmol) in THF (150 ml) over a period of 1 h. After the mixture was stirred overnight at room temperature, all volatiles were removed in vacuo. The air-sensitive residue was sublimed at 140° C./0.05 mbar to obtain 13.0 g (79.6%) of $(MeC_5H_4)Zr(C_7H_7)$ as a purple crystalline solid. Anal. calcd. for $Zr_1C_{13}H_{14}$: C: 33.65; H: 6.35. Found: C: 26.963; H: 5.03. Mp. 174-176° C., $^1$H NMR $(C_6D_6)$ 1.81 (s, 3H, CH$_3$), 5.14 (t, 2H, CH)), 5.23 (m, 2H, CH) 5.24 (s, 7H, CH); $^{13}C\{^1H\}$ NMR $(C_6D_6)$ 14.61 (CH$_3$), 41.74 (Cp ring), 81.39 (C$_7$-ring), 100.92 (Cp ring), 103.34 (Cp ring). MS (EL 70 eV) m/z: 260 (M$^+$) with the correct isotopic distribution.

FIG. 1 shows the structure of (MeCp)ZrCHT and FIG. 2 provides the TGA curve measured for this compound. (MeCp)ZrCHT is a solid precursor at 100° C.

Example 3

The thermal stability of the CpTiCHT synthesized in Example 1 was tested on an extremely high surface area silica substrate and found to be good. The compound saturated the silica surface at 400° C., although the ligands are most likely decomposed. CpTiCHT was observed to be a blue solid that vaporized at 130° C.

Example 4

Figure 3A:
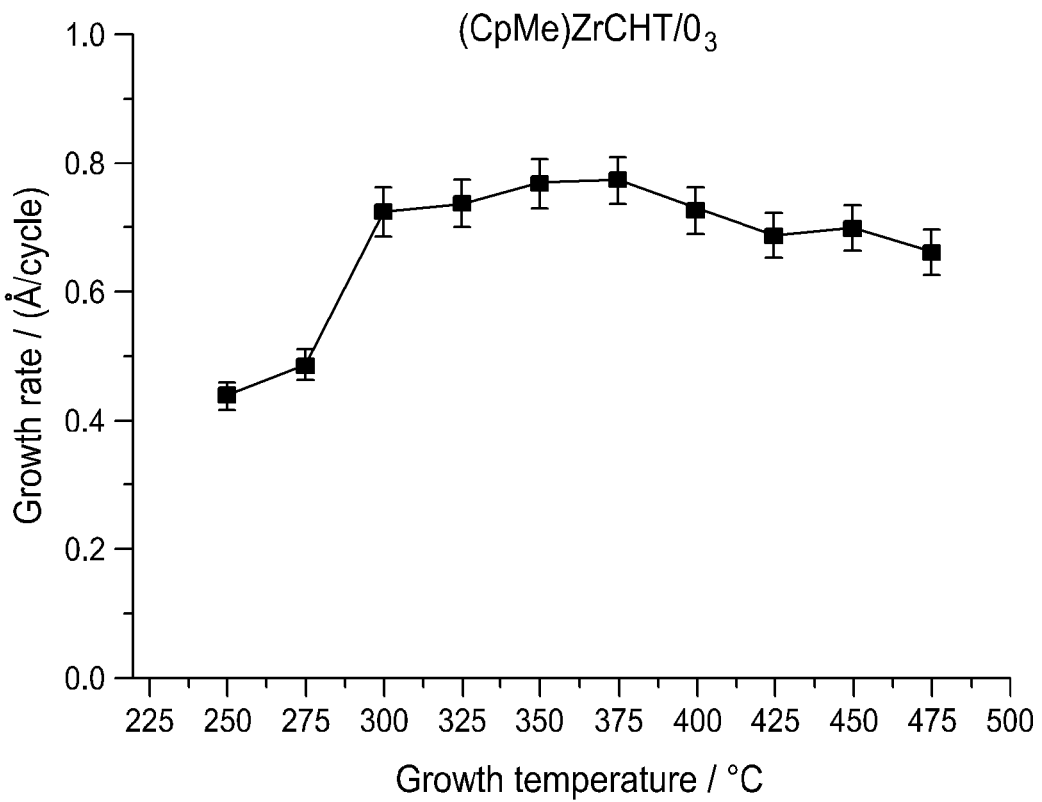
FIGS. 3A and 3B are graphs of growth rate at various temperatures (FIG. 3A) and saturation as measured by growth rate for different metal reactant pulse lengths (FIG. 3B).
Figure 3B:
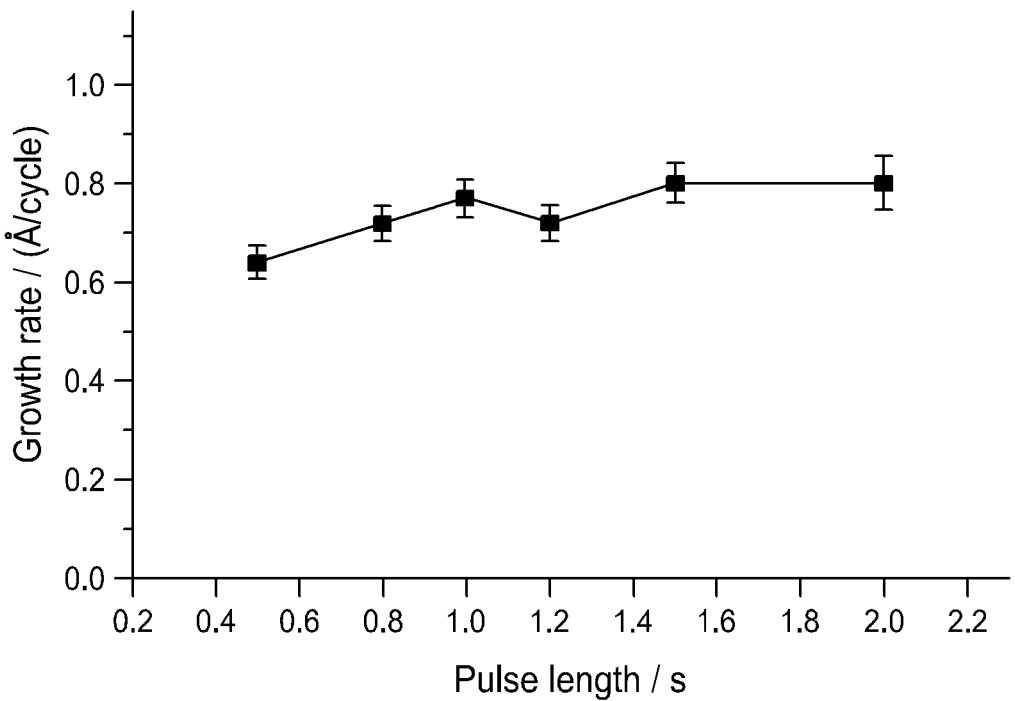
Figure 5A:
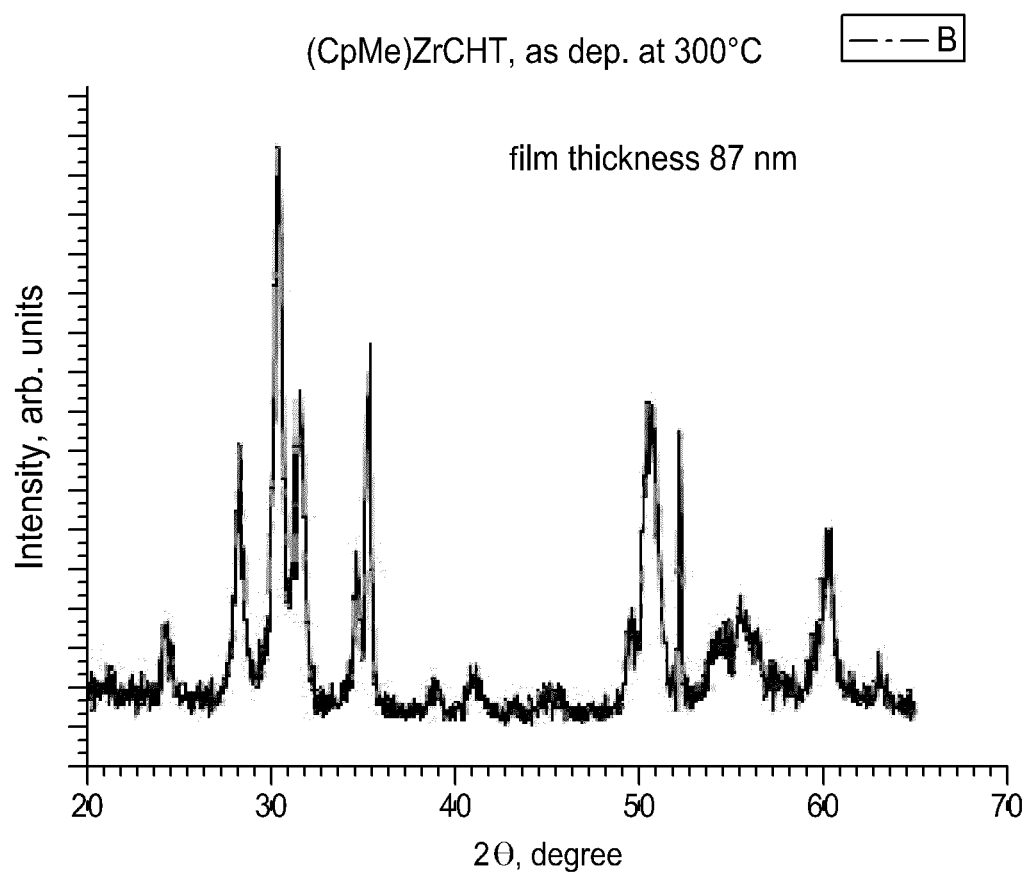
FIGS. 5A, 5B and 5C show XRD data for $ZrO_2$ films deposited using (MeCp)ZrCHT and $O_3$ at various temperatures.
Figure 5B:
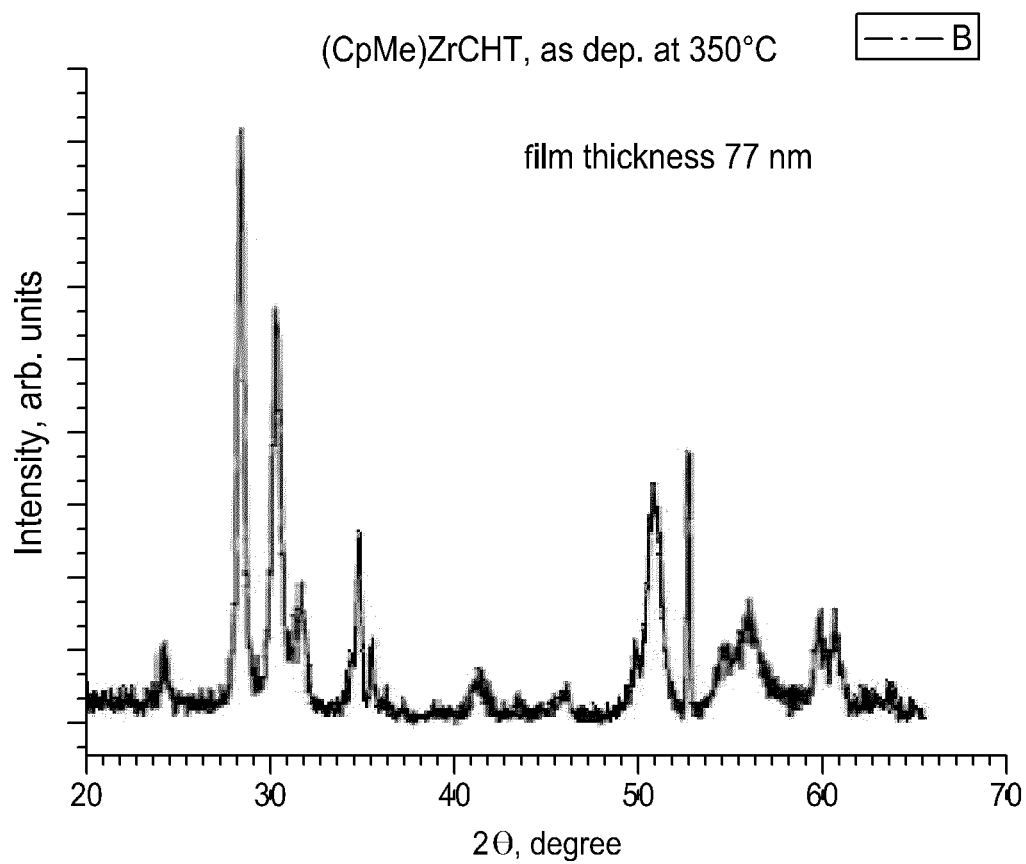
Figure 5C:
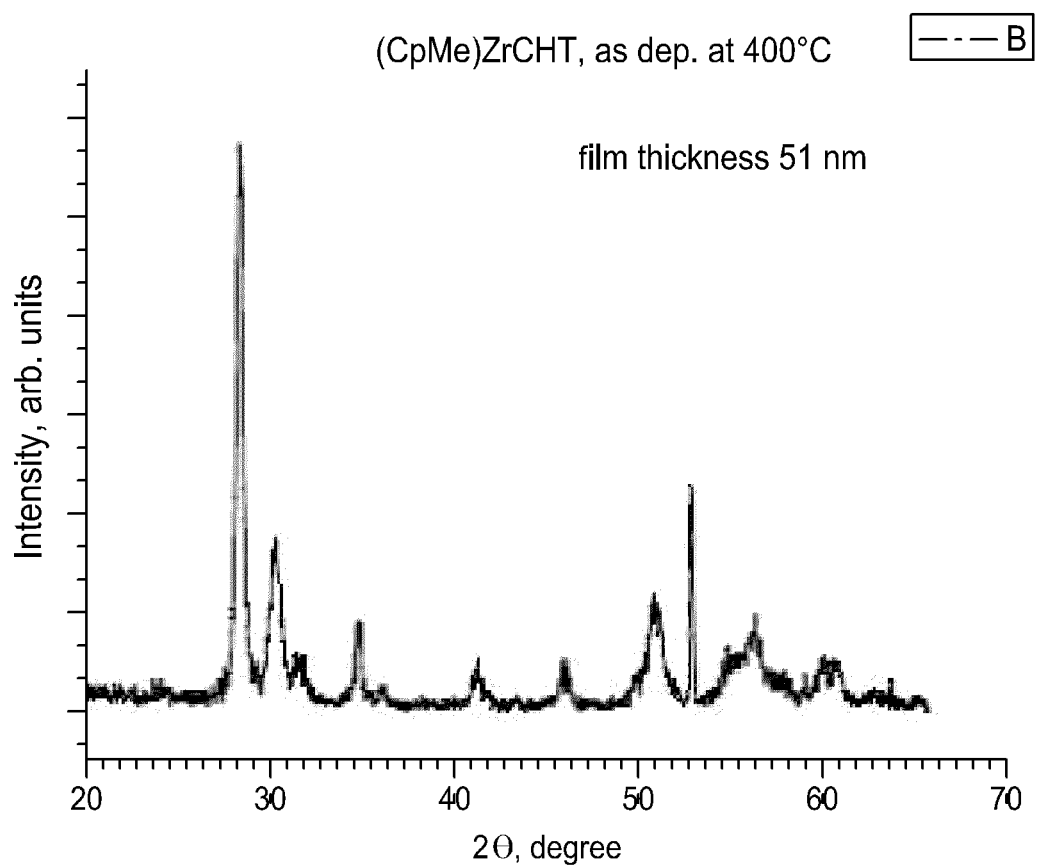
Figure 6:
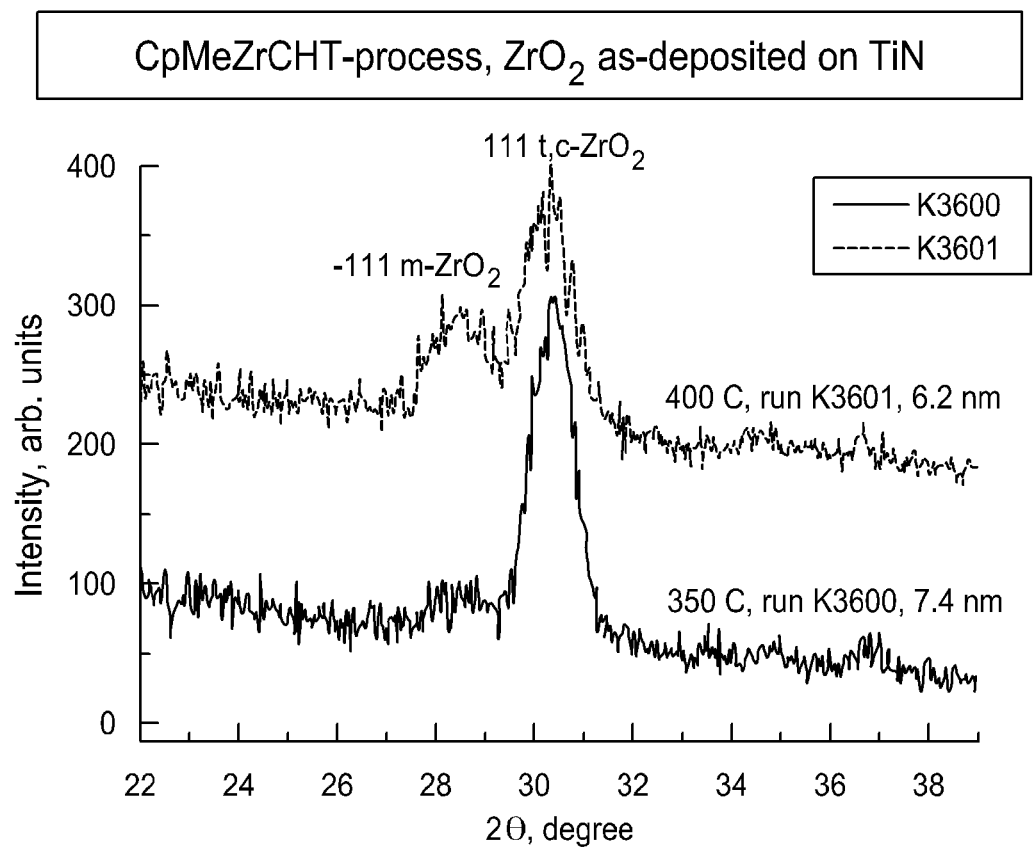
FIG. 6 represents graphs of GIXRD data for $ZrO_2$ films deposited using (MeCp)ZrCHT and $O_3$.

(MeCp)ZrCHT was synthesized as described above. (MeCp)ZrCHT was used in combination with O$_3$ in an ALD process essentially as described herein. An ozone concentration of 100 g/m$^3$ was used. Smooth, uniform zirconium oxide films were deposited at temperatures up to about 450° C. Saturation was confirmed at 350° C., and at 400° C. only slight decomposition was observed as the growth rate increased from 0.7 Å/cycle with 1 s pulses of the metal precursor to 0.8 Å/cycle with 2 s pulses. FIG. 3. According to ERDA, the films deposited at 350° C. were exceptionally pure (no H detected, <0.06 at. % C). FIG. 4. XRD data is presented in FIGS. 5a, 5b and 5c. GIXRD data is presented in FIG. 6. Similar characteristics were observed as with films deposited from (CpMe)$_2$Zr(OMe)Me and O$_3$.

Figure 7:
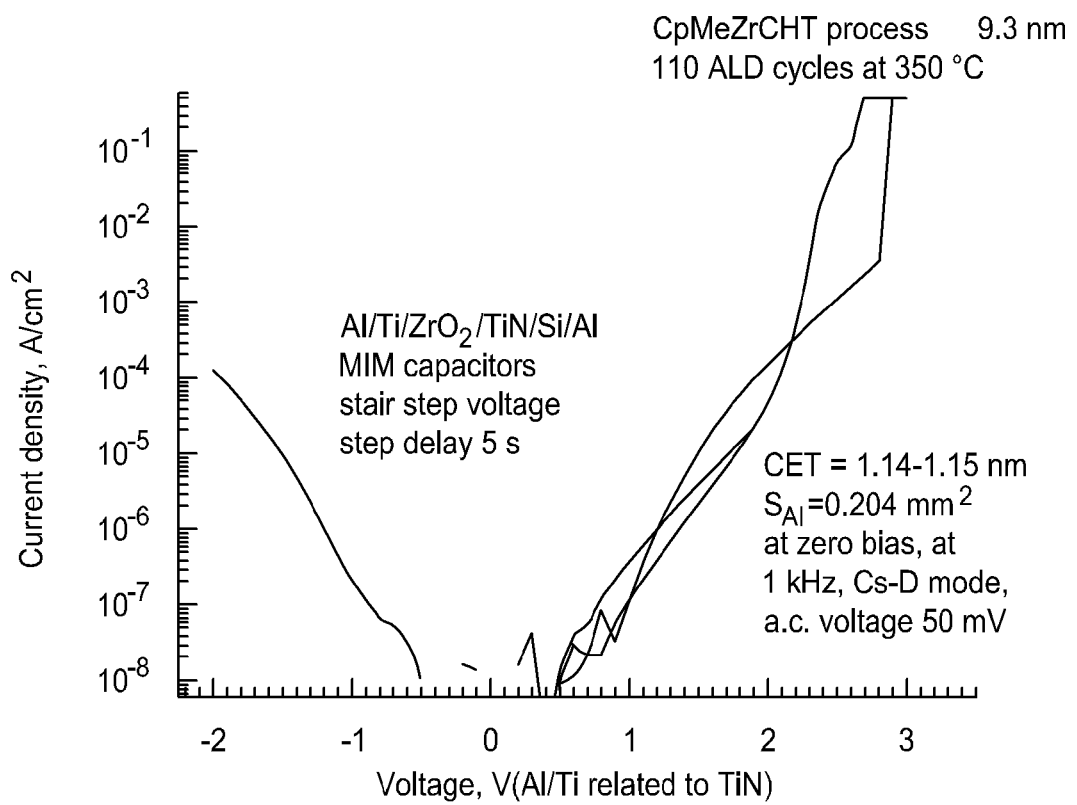
FIG. 7 illustrates experiments to characterize the electrical properties of $ZrO_2$ films deposited using (MeCp)ZrCHT and $O_3$.

Several of the deposited ZrO$_2$ films were tested for their electrical properties. Preliminary results shown in FIG. 7 verify that the films act as dielectrics. A film deposited at 400° C. showed a CET of 0.67-1.17 nm (6.2 nm/5.58 g/cm3).

Example 5

ZrO$_2$ is deposited by ALD from alternating pulses of (MeCp)ZrCHT or another CHT metal precursor and an oxygen source, such as O$_3$ The substrate temperature is above 300° C.

Example 6

HfO$_2$ is deposited on a substrate by ALD using alternating pulses of a Hf CHT precursor and an oxygen source, such as O$_3$ at a substrate temperature of above 300° C.

Example 7

TiO$_2$ is deposited on a substrate by ALD using alternating pulses of CpTiCHT and O$_3$ at a substrate temperature of above 300° C.

Example 8

Figure 9:
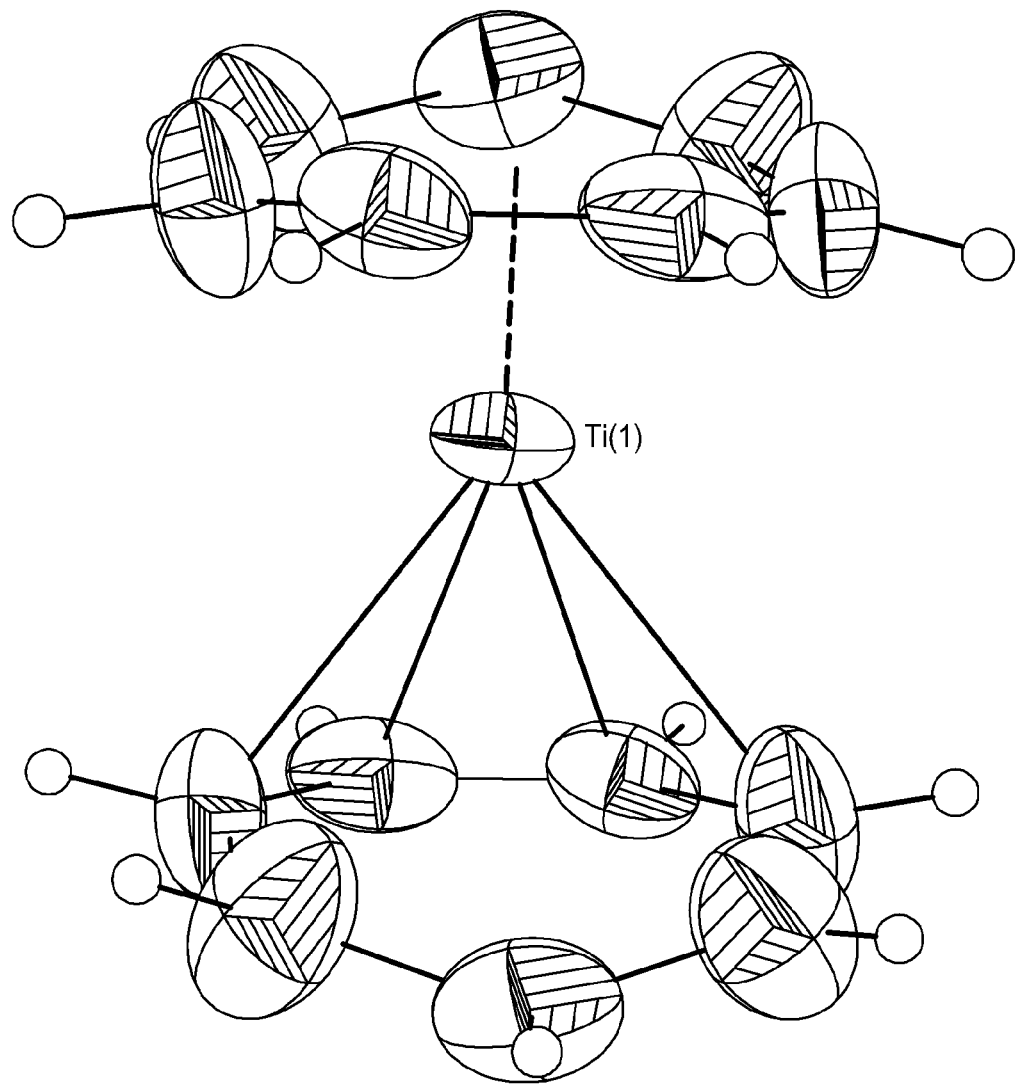
FIG. 9 is a schematic of the crystal structure of $Ti(C_7H_8)_2$. The formulation may also be $(C_7H_7)Ti(C_7H_9)$ i.e. (CHT)Ti(CHD).
Figure 10:
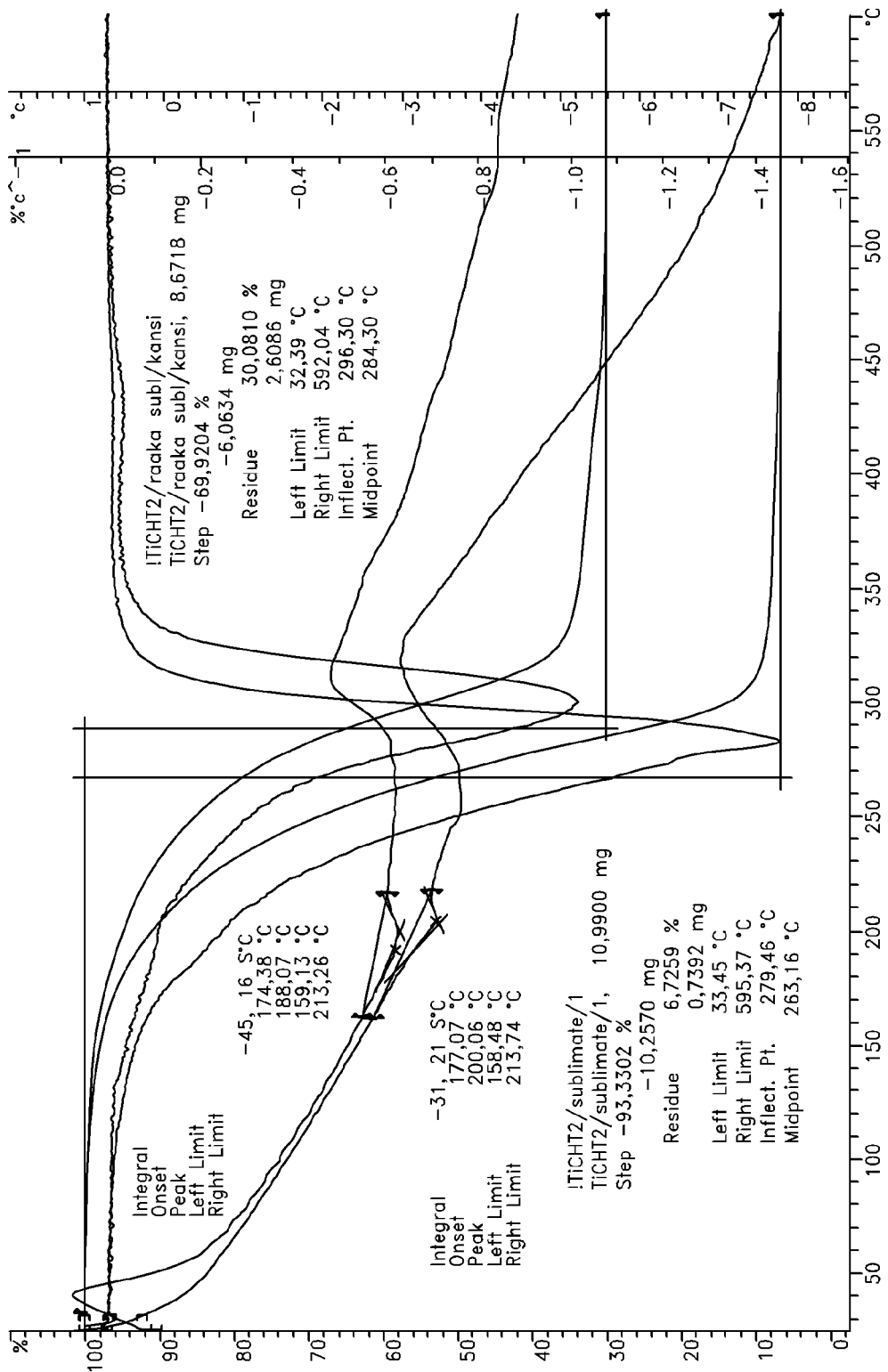
FIG. 10 shows TG, DTG and SDTA curves measured for (CHT)Ti(CHD).

Synthesis of CHT metal reactant: In a 1-L flask containing 5 g of magnesium chips were added 0.5 g of anhydrous FeCl$_3$, 30 ml of cycloheptatriene, 30 ml of THF, and, over a 1-h period to allow the warming of the stirred reaction mixture, a solution of 12 g (0.063 mol) of TiCl$_4$ in 200 ml of THF. The mixture was stirred at room temperature over night, and the volatile products were evaporated under vacuum. Sublimation of the residue (130° C./0.05 mmHg) gave a dark solid: 24.4% yield (3.54 g); mp. 177-200° C.; $^1$H NMR (C6D6): 1.2-1.5 (m, CH), 1.9-2.1 (m, CH), 2.1-2.2 (m, CH), 4.2-4.4 (m, CH), 4.9-5.1 (CH, m), 5.32 (s, 7H, CH), 5.6-5.8 (m, CH); 13C$\{1H\}$ NMR (C6D6): 37.34 (CH, C7-ring), 88.67 (CH, η7-C7-ring), 101.53 (CH, C7-ring), 102.33 (CH, C7-ring), 113.39 (CH, C7-ring); MS (EI, 70 eV) m/z: 278, 232, 230 [M]+, 91 [C7H7]+. The chemical structure of the synthesized CHT compound was determined to be (C$_7$H$_7$)Ti(C$_7$H$_9$)/Ti (C$_7$H$_8$)$_2$. While this is believed to be accurate, identification of the structure was difficult and it was initially identified differently. Crystal structure of the synthesized precursors is shown in FIG. 9. TG, DTG and SDTA curves measured for (CHT)Ti(CHD) are shown in FIG. 10.

Other transition metals precursors of formula (III), such as $(C_7H_7)M(C_7H_9)/M(C_7H_8)_2$, where M is a transition metal, preferably group IVB metal such as Ti, Zr, Hf, can be synthesized using essentially the method described above for synthesis of $(C_7H_7)Ti(C_7H_9)/M(C_7H_8)_2$.

It will be appreciated by those skilled in the art that various modifications and changes can be made without departing from the scope of the invention. Similar other modifications and changes are intended to fall within the scope of the invention, as defined by the appended claims.

We claim:

1. A method for forming a zirconium oxide thin film on a substrate comprising:
    alternately and sequentially contacting the substrate with a vapor phase first zirconium reactant and a vapor phase second oxygen reactant until a thin zirconium oxide film of a desired thickness and composition is obtained,
    wherein the first zirconium reactant comprises at least one ligand comprising a C7 ring structure.

2. The method of claim 1, wherein the first zirconium reactant is an organometallic reactant.

3. The method of claim 1, wherein the first zirconium reactant comprises at least one cycloheptatrienyl (CHT) ligand.

4. The method of claim 3, wherein the first zirconium reactant comprises two ligands, one of which is the CHT ligand.

5. The method of claim 4, wherein the first zirconium reactant comprises two CHT ligands.

6. The method of claim 3, wherein the first zirconium reactant comprises one CHT ligand and one cycloheptadienyl (CHD) ligand.

7. The method of claim 3, wherein the first zirconium reactant comprises (CHT)ZrNR, where R is $Me_2$, MeEt or $Et_2$.

8. The method of claim 1, wherein the first zirconium reactant is $(C_7H_7)Zr(C_7H_7)$.

9. The method of claim 1, wherein the first zirconium reactant is $(C_7H_7)Zr(C_7H_9)$.

10. The method of claim 1, wherein the substrate temperature when contacted with the first and second reactants is above about 350° C.

11. The method of claim 1, wherein the first zirconium reactant does not comprise a halide.

12. The method of claim 1, wherein the second oxygen reactant is selected form oxygen, oxygen plasma, atomic oxygen, ozone, water, NO, $NO_2$, $N_2O$ and $H_2O_2$.

13. The method of claim 12, wherein the second oxygen reactant comprises oxygen plasma.

14. The method of claim 13, wherein the oxygen plasma is generated in situ.

15. The method of claim 13, wherein the oxygen plasma is generated remotely.

16. An atomic layer deposition process for forming a zirconium oxide thin film on a substrate in a reaction space comprising multiple zirconium oxide deposition cycles, each deposition cycle comprising, alternately:
    contacting the substrate with a first vapor zirconium reactant; and
    contacting the substrate with a second vapor phase oxygen reactant;
    wherein the deposition cycle is repeated until a zirconium oxide thin film of a desired thickness and composition is obtained, and wherein the first zirconium reactant comprises a C7 ring structure and an amide and the second reactant comprises an activated or excited oxygen species.

17. The method of claim 16, wherein the first zirconium reactant comprises at least one cycloheptatrienyl (CHT) ligand.

18. The process of claim 17, wherein the first zirconium reactant comprises (CHT)ZrNR, where R is $Me_2$, MeEt or $Et_2$.

19. The method of claim 16, wherein the second reactant comprises oxygen plasma or ozone.

20. The method of claim 16, wherein the substrate temperature is above about 300° C.

21. The method of claim 1, wherein the first reactant comprises at least one substituted or unsubstituted cyclopentadienyl (Cp) ligand.

22. The method of claim 21, wherein the first reactant comprises at least one cycloheptatrienyl (CHT) ligand.

23. The method of claim 16, wherein the first zirconium reactant comprises at least one substituted or unsubstituted cyclopentadienyl (Cp) ligand.

* * * * *